United States Patent
Crowley

[11] Patent Number: 6,074,349
[45] Date of Patent: Jun. 13, 2000

[54] ACOUSTIC IMAGING AND DOPPLER CATHETERS AND GUIDEWIRES

[75] Inventor: Robert J. Crowley, Wayland, Mass.

[73] Assignee: Boston Scientific Corporation, Watertown, Mass.

[21] Appl. No.: 08/909,414

[22] Filed: Aug. 11, 1997

Related U.S. Application Data

[63] Continuation of application No. 08/659,023, Jun. 4, 1996, Pat. No. 5,655,537, which is a continuation of application No. 08/347,284, Nov. 30, 1994, abandoned.

[51] Int. Cl.[7] .................................. A61B 8/00; A61B 8/06
[52] U.S. Cl. .......................... 600/463; 600/465; 600/468
[58] Field of Search .................................. 600/455, 439, 600/461–463, 468, 465–467

[56] References Cited

U.S. PATENT DOCUMENTS

| | | | |
|---|---|---|---|
| 4,276,491 | 6/1981 | Daniel | 128/662.04 |
| 4,869,258 | 9/1989 | Hetz | 600/446 |
| 4,870,972 | 10/1989 | Maerfeld et al. | 128/662.03 |
| 4,915,115 | 4/1990 | Sasaki et al. | 128/662.04 |
| 4,951,677 | 8/1990 | Crowley | 128/662.06 |
| 5,000,185 | 3/1991 | Yock | 128/662.03 |
| 5,121,749 | 6/1992 | Nassi et al. | 128/692 |
| 5,226,421 | 7/1993 | Frisbie et al. | 128/622.04 |
| 5,246,007 | 9/1993 | Frisbie et al. | 128/622.06 |
| 5,351,693 | 10/1994 | Taimisto et al. | 600/465 |
| 5,363,853 | 11/1994 | Lieber et al. | 128/662.06 |
| 5,373,845 | 12/1994 | Gardineer et al. | 128/662.09 |
| 5,375,601 | 12/1994 | Nicholas et al. | 128/662.06 |
| 5,655,537 | 8/1997 | Crowley | 600/465 |

FOREIGN PATENT DOCUMENTS

| | | | |
|---|---|---|---|
| WO 92/03095 | 3/1992 | WIPO | A61B 8/12 |
| WO 93/16642 | 9/1993 | WIPO | A61B 8/12 |
| WO 93/17624 | 9/1993 | WIPO | A61B 8/12 |

OTHER PUBLICATIONS

Crowley et al., "Ultrasound Guided Therapeutic Catheters: Recent Developments and Clinical Results," International Journal of Cardiac Imaging, 6:145–156, 1991.

Crowley et al., "Optimized Ultrasound Imaging Catheters for Use in the Vascular System," International Journal of Cardiac Imaging, 4:145–151, 1989.

Bom et al., "Early and Recent Intraluminal Ultrasound Devices," International Journal of Cardiac Imaging, 4:79–88, 1989.

Crowley, "Ultrasound Catheter Imaging—A Functional Overview," SPIE, 1068:160–165, 1989.

*Primary Examiner*—Francis J. Jaworski
*Attorney, Agent, or Firm*—Lyon & Lyon LLP

[57] ABSTRACT

The invention features an acoustic medical device for making Doppler measurements and imaging within a body fluid conduit using a single-transducer. The device has an elongated device body, defining a device axis, constructed for positioning a distal end of the device body near a region of interest in the body fluid conduit. Disposed within the device body is an ultrasonic beam directing assembly that is constructed to direct a portion of ultrasonic energy from a single transducer in a direction for imaging within the body fluid conduit and to direct another portion of the ultrasonic energy in a direction for making Doppler measurements within the body fluid conduit.

25 Claims, 5 Drawing Sheets

ACOUSTIC IMAGING AND DOPPLER CATHETERS AND GUIDEWIRES

This is a continuation of application Ser. No. 08/659,023, filed on Jun. 4, 1996, and now U.S. Pat. No. 5,655,537 which is a continuation of application Ser. No. 07/347,284, filed on Nov. 30, 1994, (now abandoned), the disclosures of each being expressly incorporated hereinto by reference in their entirety.

FIELD OF THE INVENTION

This invention relates to imaging and to making doppler measurements within a body conduit using acoustic energy.

BACKGROUND OF THE INVENTION

Arteriosclerosis is a vascular disease characterized by constrictions, generally referred to as stenoses, which result from the build-up of plaque on the interior wall of a blood vessel. Platelets may aggregate on the diseased blood vessel and form clots, which further occlude the lumen.

Arteriosclerosis is commonly treated by balloon angioplasty. Prior to treatment, it is often desirable to have an accurate visual picture of the affected area or to gather blood velocity data in order to assess the obstruction. After treatment, imaging and velocity information is useful to determine whether the stenosis has been successfully removed.

Ultrasound imaging catheters and guidewires can provide an image of the intraluminal anatomy. These devices include a transducer that emits ultrasound beams in a direction generally transverse to the catheter axis. The ultrasound energy reflected from the lumen wall is detected and processed to provide the image.

Doppler flow catheters and guidewires are used to measure the velocity of fluid within a body conduit. These devices have a transducer that emits an ultrasonic beam generally along the device axis. The ultrasonic energy reelected from the flowing fluid is detected and Doppler-analyzed to determine the velocity.

Imaging and Doppler data have been obtained by delivering an imaging catheter over a Doppler guidewire or by using a catheter with multiple transducers, some of which are dedicated for imaging and some of which are dedicated for Doppler measurement. The imaging data can be processed to determine the cross sectional area of the vessel lumen. Combined with the flow velocity data from the Doppler measurement, the blood flow volume can be computed.

SUMMARY OF THE INVENTION

The invention relates to devices that use a single transducer for imaging and for obtaining Doppler data.

In a first aspect, the invention features a medical device for making Doppler measurements and imaging within a body fluid conduit using a single transducer. The device has an elongated device body, defining a device axis, constructed for positioning a distal end near a region of interest in the body fluid conduit. Disposed in the device body is an ultrasonic beam directing assembly that is constructed to direct a portion of ultrasonic energy from a single transducer in a direction for imaging within the body fluid conduit and to direct another portion of the ultrasonic energy in a direction for making Doppler measurements within the body fluid conduit.

Embodiments may include one or more of the following. A portion of the ultrasonic energy is directed in a direction that is generally transverse to the device axis for imaging within the body fluid conduit and another portion of the ultrasonic energy is directed in a direction that is generally along the device axis for making Doppler measurements within the body fluid conduit. The ultrasonic beam-directing assembly includes an ultrasonic transducer positioned with respect to an ultrasonic beam splitter, such that ultrasonic energy is directed from the transducer to the beam splitter where it is then spatially separated into a portion for providing an image of a wall of a body lumen and another portion for making Doppler measurements of the flow of fluid in the body conduit. The beam splitter is made from a partially sonolucent polymeric material and is located transversely with respect to the device axis.

Embodiments may also include one or more of the following. The partially sonolucent polymeric material forms at least a portion of the wall of the device body. The wall of the device body is shaped to efficiently direct a portion of the energy for making Doppler measurements generally along the axis of the device body. The distal end of the device body is flared such that the exit angle of the ultrasonic energy for making Doppler measurements is 15° or less with respect to the device axis. The distal end of the device body is either open or closed. If the distal end is closed, it is made from a sonolucent material.

Embodiments may also include one or more of the following. The transmissivity and reflectivity of the beam-directing assembly is varied by varying the acoustic impedance of the ultrasonic beam splitter. The impedance of the ultrasonic beam splitter is varied by flowing fluids of varying impedance behind the ultrasonic beam splitter. The impedance of the ultrasonic beam splitter is varied by varying the thickness of the partially sonolucent beam directing material.

Embodiments may also include an analysis circuit that includes a timing circuit and a switch such that the ultrasonic imaging signal, from the portion of ultrasonic energy for imaging, is differentiated from the ultrasonic Doppler signal, from the other portion of ultrasonic energy for making Doppler measurements, by a time delay between these signals. The ultrasonic imaging signal and the Doppler signal are separately analyzed using imaging and Doppler electronics.

Embodiments may also include one or more of the following. The beam directing assembly is an acoustically reflective ring disposed within the device body where a portion of the device body is formed from a sonolucent material. The transducer is mounted on a hinge that is constructed to permit the transducer to rotate between at least two angles. The transducer has two facets that are mounted on it such that the transducer emits ultrasonic energy in two spatially separate directions simultaneously.

In another aspect, the invention features a method for making Doppler measurements and imaging within a body fluid conduit by introducing a medical device into a patient's body fluid conduit, the medical device having an ultrasonic transducer and an ultrasonic beam-directing assembly near its distal end, positioning the distal end of the device near a region of interest within the body fluid conduit, directing ultrasonic energy from the transducer in a first direction for imaging within the body fluid conduit and in a second, different direction for making Doppler measurements within the body fluid conduit, and receiving the reflected signals back containing the image and flow information. The ultrasonic beam-directing assembly is an ultrasonic beam splitter which spatially separates the ultrasonic signal from the transducer into one portion for providing an image of a wall of the body fluid conduit and another portion for making Doppler measurements of the flow of fluid in the body fluid conduit.

The inventions have many advantages. The systems may use a single transducer for imaging and for Doppler measurements. This feature simplifies the design of the devices, permits low profiles, reduces electrical and acoustic interferences, and enables both imaging and Doppler flow data to be taken from substantially the same location in a vessel, in some embodiments, simultaneously. These advantages, particularly making imaging and Doppler measurements from substantially the same location at substantially the same time, can allow highly accurate blood flow volume measurements to be made easily and in a short time.

Other aspects, features, and advantages follow.

DESCRIPTION OF THE PREFERRED EMBODIMENTS

Figures 1, 1A:
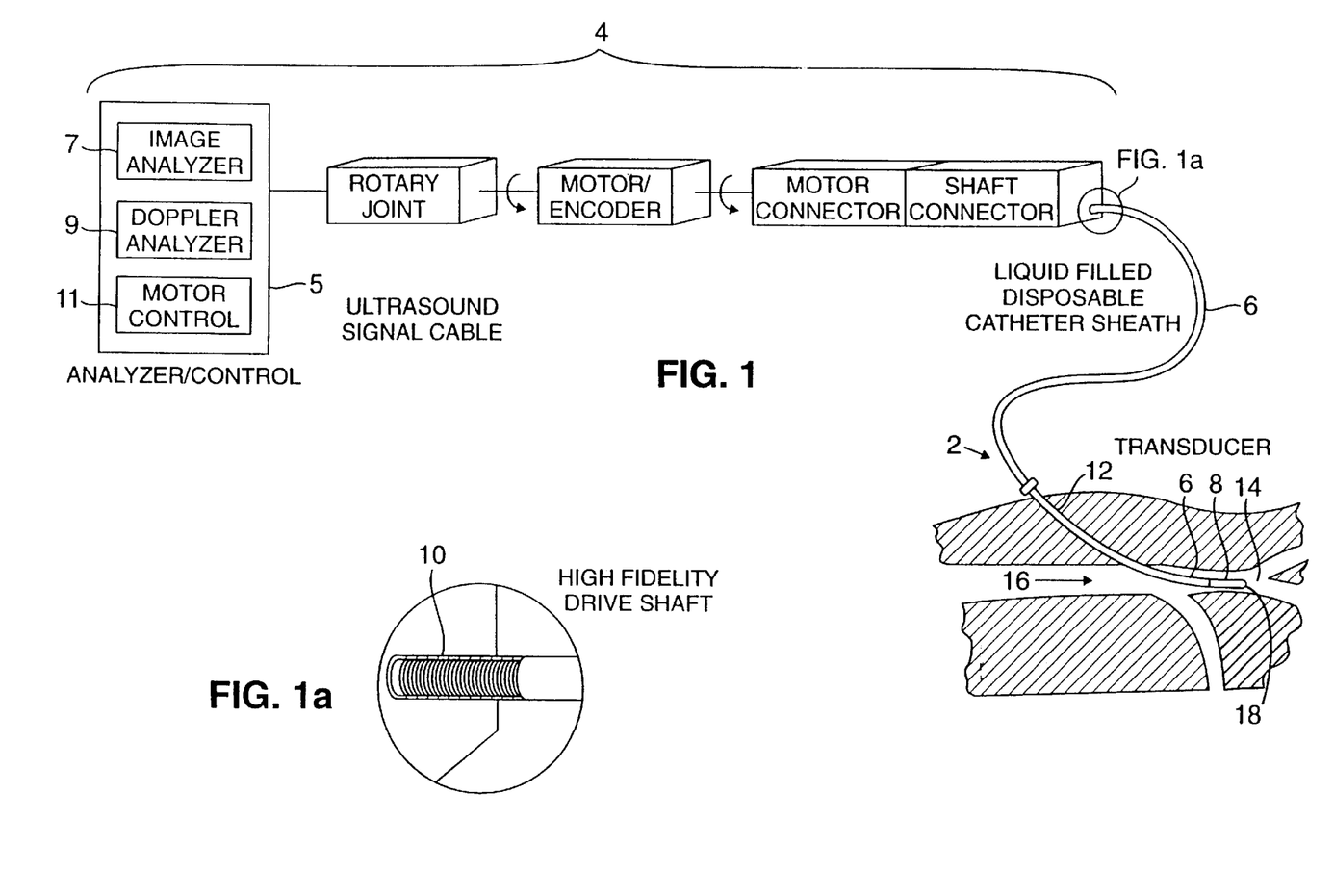
FIG. 1 is a schematic of an acoustic system according to the invention.

Referring to FIG. 1, an acoustic system includes a catheter 2 that is driven by a control system 4. The control system 4 includes an analyzer/controller unit 5 with both an image analyzer 7 and a Doppler analyzer 9. The catheter 2 has a disposable catheter sheath 6 including a disposable, miniature, rotatable ultrasonic transducer 8 driven by a high fidelity flexible drive shaft 10. (Alternatively, the transducer can be mounted on a flexible member that need not be rotatable). The catheter is adapted to be positioned in the body by a standard catheter procedure. For example, a catheter may be delivered within a blood vessel or the heart by guiding a flexible catheter along a circuitous path, starting with percutaneous introduction through an introducer sheath 12 disposed in a perforation of the femoral artery 14. The distal end of the acoustic catheter 2 is positioned within artery 14 such that blood flows in the direction of arrow 16. A distal end of the catheter sheath, corresponding to the location of the transducer, is constructed from an acoustically transmissive material, such as, for example, low-density polyethylene, which has an acoustic impedance of about 1.8 MRayles, for example, 1.76 MRayles. The proximal end of the catheter is connected by a mating system to the control system 4. The control system 5 also includes motor control 11 for controlling the rotation of a transducer. The transducer may have a concave surface for focusing the acoustic energy. The sheath and drive shaft are of the type described in detail in U.S. Pat. No. 4,951,677, the entire contents of which are incorporated herein by reference.

Figure 2:
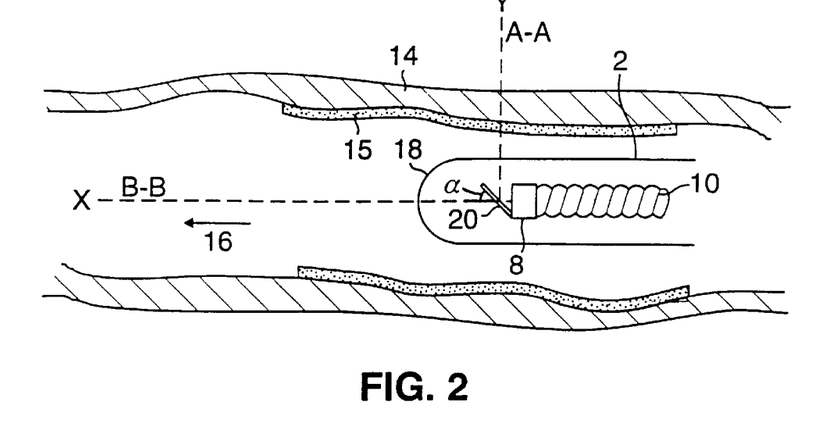
FIG. 2 is an enlarged cross-sectional view of the distal end of the acoustic catheter in FIG. 1 in a body lumen.

Referring to FIG. 2, the distal end of acoustic catheter 2 is positioned within the artery 14 to collect image and flow information at a location where plaque 15 has formed on the vessel wall. The distal end includes transducer 8 which is driven by rotatable drive shaft 10 and positioned opposite an acoustic beam splitter 20. Transducer 8, operating at a frequency of about 20 MHz, propagates ultrasonic sound waves in a beam which impinges upon beam splitter 20. The beam splitter 20 spatially separates the ultrasound energy into two beam components by reflecting some energy transversely, along line A—A, and permitting the remainder of the energy to continue axially along line B—B. Line A—A illustrates the path of the tomographic imaging portion of the beam as it is propagated and reflected from splitter 20, through the catheter 2, to the vessel wall region of interest "Y." (The path of line A—A may be altered by decreasing the angle between line A—A and the longitudinal axis of catheter 2 and still obtain the imaging information). Line B—B shows the path of the Doppler flow measurement portion of the beam which propagates through the beam splitter 20 to the region of interest "X," which is generally a distance beyond the tip of the catheter so that vortices created by blood flow at the tip do not interfere with the velocity measurement. Notably, there is a substantial difference between the distances A—A and B—B.

In particular embodiments, the beam splitter 20 is oriented at approximately a 40 to 45 degree angle, angle α, with respect to the longitudinal catheter axis and is made of a material that has a slight but significant acoustic impedance mismatch with aqueous media (saline, blood). The material reflects a significant portion of the acoustic beam transversely while also transmitting a substantial portion of the beam so that it propagates axially. For example, the beam splitter may be formed of a sheet of high density polyethylene having an acoustic impedance of about 2.3–2.4 MRayles. The thickness of the sheet is generally greater than one half of a wavelength of the acoustic energy, for example about 0.005 inch, so that the acoustic mismatch is substantial. The sheet may be placed on a frame-like support that is attached to, and rotates with, the transducer assembly. In a typical case, the length of line A—A to the imaging region "Y" is less than about 5 mm, typically about 2.5 mm. The distance along line B—B, to the Doppler region "X" is typically less than about 1 cm, for example about 5 mm, from the tip of the catheter. The distal tip 18 of the catheter 2 may be closed with a sonolucent material, such as low density polyethylene. To further reduce impedance mismatch of the catheter body, the catheter 2 may be filled with water, saline, blood, or oil. Alternatively, the distal tip 18 of the catheter is left open so that the back of the beam splitter is exposed to the body fluid. This arrangement has the advantage of eliminating any impedance mismatch at the distal tip of the catheter. Saline or other solutions can also be flushed through the catheter such that it exits the open distal end.

Figure 3:
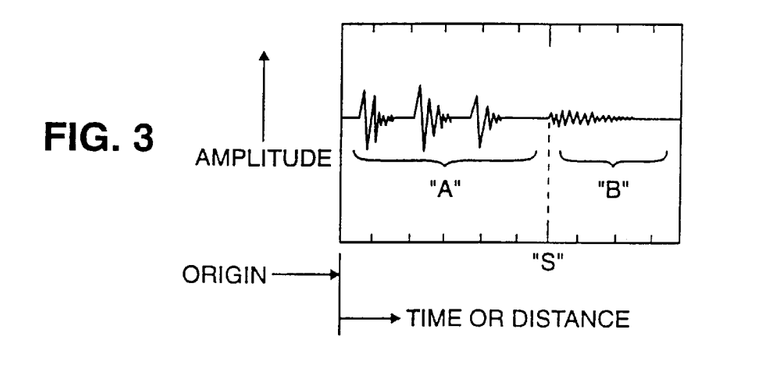
FIG. 3 is a schematic illustration of an oscilloscope of detecting signals returned from the regions of interest in FIG. 2.

Referring to FIG. 3, the signals returning from the regions of interest "X" and "Y" are separated in time, as illustrated schematically on an oscilloscope tracing. Signal segment A, which is received first in time, contains the reflected imaging tomographic information. Signal segment B, which is detected later in time, contains the reflected Doppler data. The signal segments are then directed to imaging and Doppler analysis circuitry.

Figure 4:
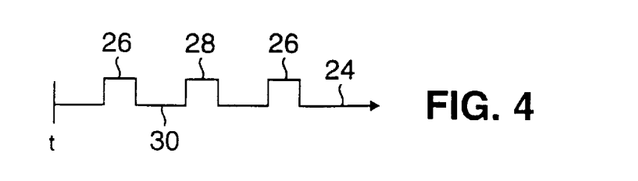
FIGS. 4 and 4A are, respectively, a schematic of a pulse train and a diagram of switching electronics for detecting image and Doppler data.
Figure 4A:
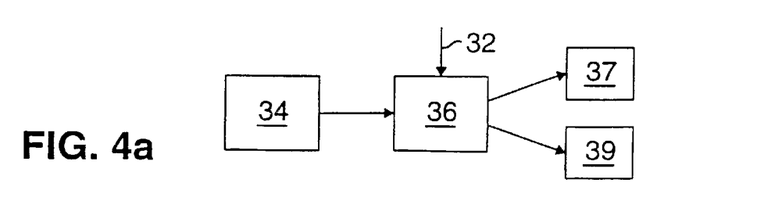

Referring as well to FIGS. 4 and 4A, the controller unit may include a CPU 34 which controls a receiver/switch 36 to connect to either imaging circuitry 37 or Doppler circuitry 39. The CPU can provide a train 24 (FIG. 4) of pulses to operate receiver/switch 36 to direct the returning signals 32 ("A" and "B") alternately to the image analysis circuitry 37 or to the Doppler analysis circuitry 39. For example, since sound waves reflected from the region closest to the transducer, imaging region "Y," return to the transducer first, timing pulse 26 from the CPU provides the timing information which then controls receiver/switch 36 to direct the returning signal "A" to the imaging analysis circuitry 37 ("t" represents time 0). Sound waves reflected from the region "X," which is further from the transducer, are detected at a later time and pulse 28 provides the timing information to receiver/switch 36 to direct the returning signal "B" to the Doppler analysis circuitry 39. (This switching occurs by time "S" in FIG. 3). Between timing pulse 26 and 28 is deadspace 30 (or a waiting period). Since the returning signal "B" directed to the Doppler analysis circuitry, the reflected flow information, is at least 5–10 decibels below the weaker echoes used for imaging information, amplification for the signals directed to the Doppler analysis circuitry must be greater than the amplification for the signals directed to the imaging analysis circuitry.

Figure 5:
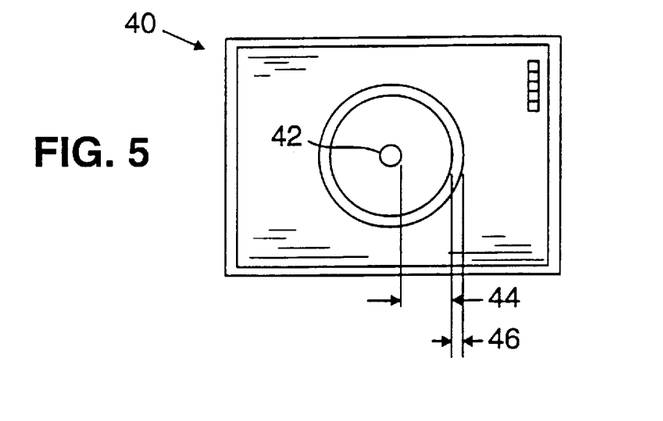
FIG. 5 is a schematic of a video screen representation of acoustic imaging and Doppler data.

Referring to FIG. 5, the returning imaging and Doppler signals may be directed to both circuitries simultaneously and the data can be displayed on an ultrasound catheter imaging screen 40. The screen displays a 360° tomogram or image that is derived from the ultrasound imaging data. The image also represents a time display. In the center of the image, an origin point 42 represents the time and spatial origin of the acoustic energy from the transducer. The radial distance from the origin 42 represents the time it takes the acoustic energy to propagate from the transducer to a location of interest and then back to the transducer. Imaging band 44 begins immediately beyond origin 42 and extends outward through the area of interest and represents the amplitude and position information of the ultrasound image. When the Doppler information is fed through the imaging analysis circuitry, Doppler band 46 appears beyond the image band 44 and typically appears as a white ring. Displaying Doppler band 46 gives the physician an intuitive picture of the amount of flow or the strength of the signal returning from the Doppler location. Specifically, Doppler band 46 (the white ring) will brighten when blood flow is sluggish since red blood cells aggregate more readily when blood flow is slowed resulting in a higher reflectivity of the acoustic energy. Additionally, slowing the scan rate (the rotation rate of the transducer) such that it is synchronized with the pulse rate, i.e., 1 cycle=1 cardiac cycle, causes light and dark bands to form on the screen which correspond to a patient's heartbeat. Further, forward, and even retrograde flow, may be represented on this band. Alternatively, the Doppler band 46 may not be displayed on the imaging screen 40. Instead, numerical or other graphic representation of velocity or volume flow can be provided.

The blood flow volume can indicate not only whether blood flow has been restored within a vessel but also to determine how much blood flow is actually reaching tissue or muscle. For example, in the coronary arteries, it is important to determine how much oxygen rich blood is being delivered to the heart muscle. Thus, after a stenosis has been dilated using a particular therapeutic technique, it is important to make sure that the blood flow has been restored. If blood flow has not been restored, a physician will know to take additional measures, such as, for example, looking for and treating another stenosis within a vessel or treating the patient temporarily with nitroglycerin, for example, to keep tissue and muscle viable.

Other embodiments

Figure 6:
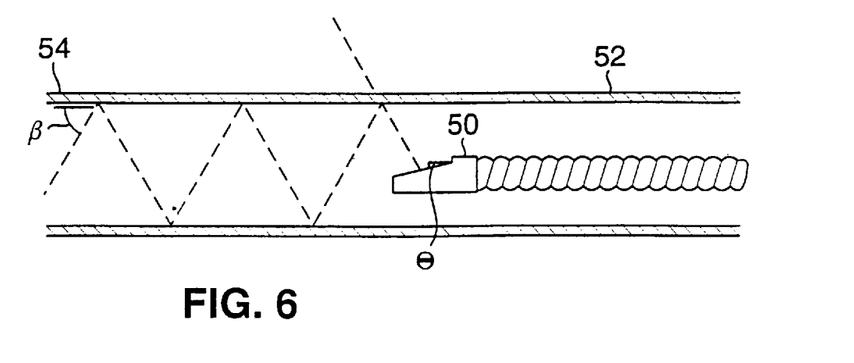
FIGS. 6–13 are enlarged cross-sectional views of the distal portion of alternative embodiments of the invention.

Referring to FIG. 6, in an alternative embodiment, a beam splitter is made integral with the catheter body wall 52 by forming the wall of partially sonolucent material, such as, for example, polyethylene, and providing a transducer 50 that emits energy at an appropriate angle toward the wall. The transducer 50 is canted slightly, to angle θ, so that a portion of the acoustic energy passes through the catheter wall 52 and a portion of the acoustic energy is multiply reflected from the inner wall of the catheter until it reaches the distal end, after which the energy propagates to the region where Doppler data is taken. The cant angle is selected to avoid the pseudo Brewster angle, the angle at which total internal reflection of the beam occurs, and to avoid near total transmission through the wall. The system can be constructed to minimize the number of internal reflections by placing the transducer sufficiently close to the distal tip 54 of the catheter. Additionally, to increase the amount of energy exiting the end of the catheter, to enhance the ability to detect the Doppler information, both the cant angle, angle θ, and the exit angle, angle β, can be optimized. Preferably the cant angle θ is about 8 to 12 degrees, and the exit angle β is about 12 to 15 degrees.

Figure 7:
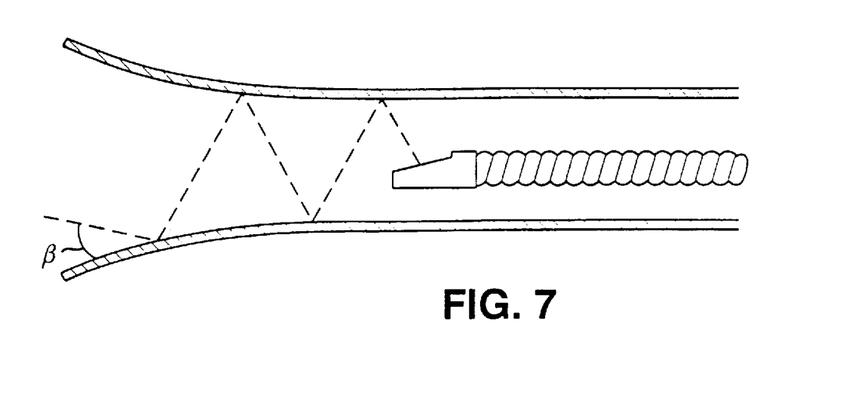

Referring to FIG. 7, in another embodiment, the end of the catheter can be flared. The flared end causes the direction of the acoustic energy exiting the catheter to change such that the exit angle β is decreased, which enhances the ability to detect the Doppler information by propagating acoustic energy in a direction along the device axis as it enters the catheter.

Figure 8:
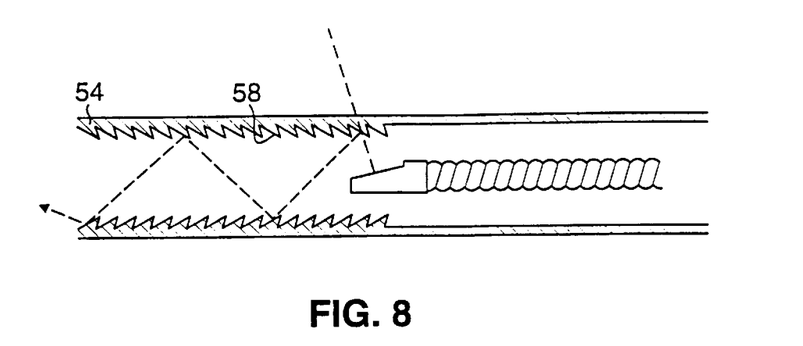

Referring to FIG. 8, in another embodiment, the interior wall 58 of the catheter can have tapered or angled ridges or may be otherwise formed in a manner so as to gradually re-direct the acoustic beam so that it exits the catheter propagating substantially along the catheter axis for obtaining the Doppler information. The catheter wall is also acoustically transmissive in order to obtain imaging information.

Figure 9:
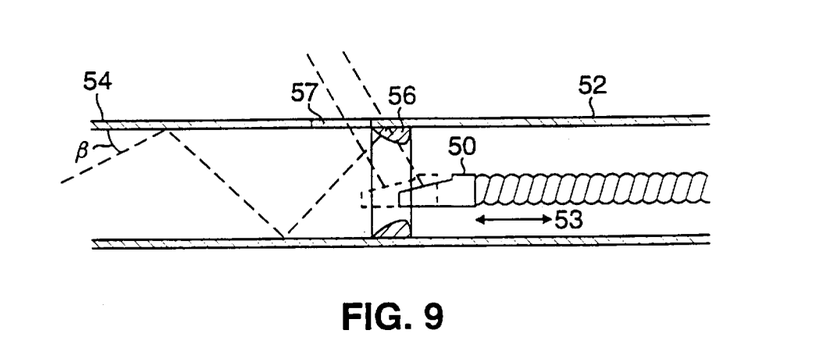

Referring to FIG. 9, in another embodiment, an acoustic reflector 56 is provided adjacent a sonolucent window 57 and an axially moveable transducer 50 is provided to alternately transmit energy for imaging and to reflect energy along the device axis for Doppler measurements. A ring reflector 56 is mounted on the wall of the catheter lumen to direct the acoustic energy in a forward direction for Doppler measurements. By sliding the transducer axially (arrow 53), either proximally or distally, the beam can be directed through a sonolucent window 57. (Alternatively, catheter wall 52 may be made from a sonolucent material). Additionally, ring reflector 56 may be made from an acoustically transmissive material so that it not only directs the acoustic energy in a forward direction for Doppler measurements, but a portion of the acoustic energy is also transmitted transversely in order to obtain the imaging information.

Figure 10:
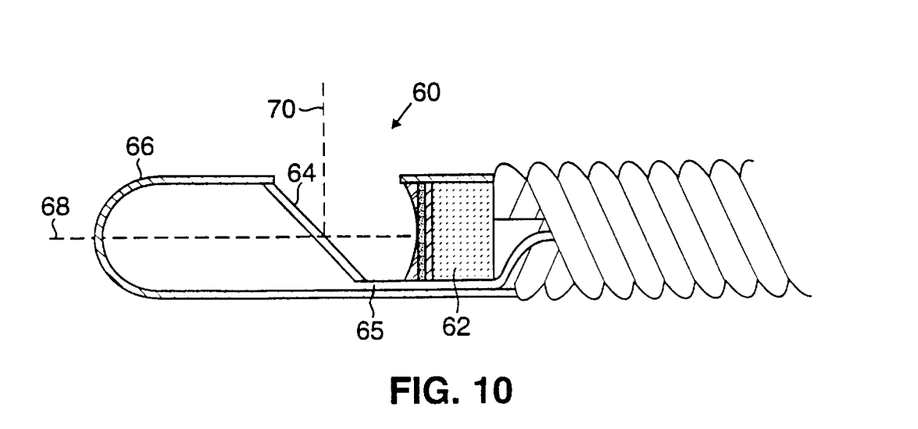

In further embodiments, an active beam splitter or beam modulator can be provided to vary the reflective and transmissive properties of the splitter. Referring to FIG. 10, a beam splitter 64 is provided opposite a transducer 62. The back surface of the beam splitter communicates with a space enclosed by a nosepiece 66. The fluid in the nosepiece can be varied to change the acoustic reflectivity of the beam-splitting mirror 64. The fluid can be changed by applying pressure or vacuum through a conduit 65. For example, when nosepiece 66 is filled with acoustically conductive material such as, for example, saline or water, some of the acoustic signals emitted from the transducer propagate along-line 68, along the axis of the catheter, to obtain Doppler information. Additionally, a portion of the acoustic signal reflects off the mirror 64 in a transverse direction, along line 70, to obtain imaging information. When the acoustically conductive materials in the nosepiece are replaced with materials, such as air, which are not acoustically matched to the mirror, or are not acoustically transmissive at the transducer's operating frequencies, total reflection on the front surface of the mirror occurs. When the acoustic signals are all reflected transversely, only imaging information can be obtained. Thus, the user can effectively switch the Doppler information on and off by changing the fluid in the nosepiece. In a typical embodiment, the acoustic mirror/beamsplitter is formed of a polymer as discussed above.

Figure 11:
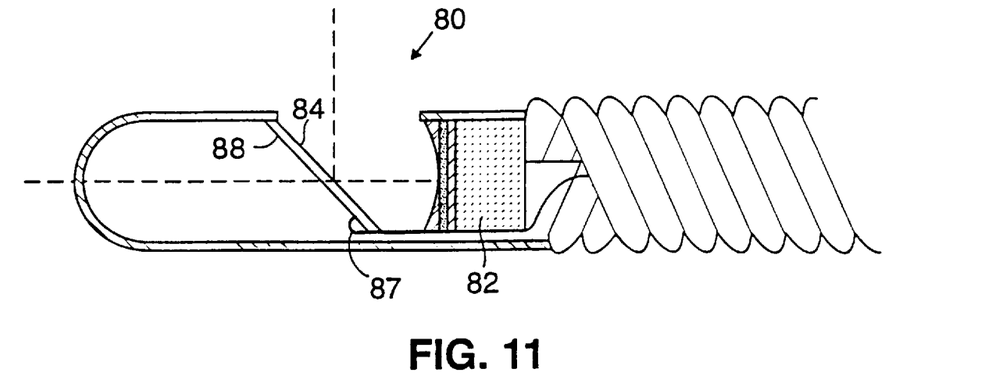

Referring to FIG. 11, an active beam splitter 80 includes a forward firing transducer 82 and a fixed splitter 84. Electrical wires 87 are connected to and disposed within the mirror, and an active film layer 88, such as, for example, a piezoelectric polymer such as polyvinylidene fluoride (PVDF), coats the back surface of the mirror. Varying the voltage on wires 87 has the effect of either increasing or decreasing the thickness of active film layer 88, which alters the impedance of the mirror system by either increasing or decreasing the transmissivity of acoustical signals. Alternatively, thin (5 microinches) metallized layers (not shown) may be disposed on both sides of mirror 84. The change in the acoustic length of the mirror may additionally attenuate either the higher or lower acoustic frequencies, resulting in a frequency modulation of the ultrasonic energy by narrowing the bandwidth of the transmitted beam.

Figure 12:
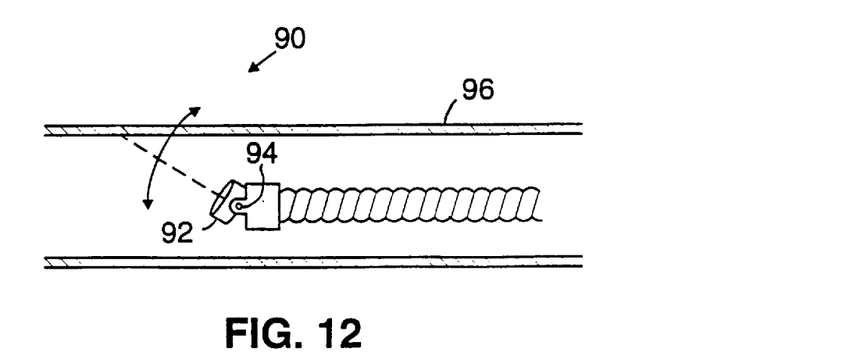

Referring to FIG. 12, in another embodiment, the angle of a single transducer is varied to alternately in time to obtain imaging and Doppler information. An acoustic catheter 90 includes transducer 92, which is articulated on a hinge 94 within the catheter 96. The transducer can be rotated about the hinge 94 either mechanically with the use of a tension wire, for example, or automatically through the use of a motor, to alter the orientation of the transducer so that it emits acoustic energy either transversely, to obtain imaging information, or axially, to obtain Doppler information.

Figure 13:
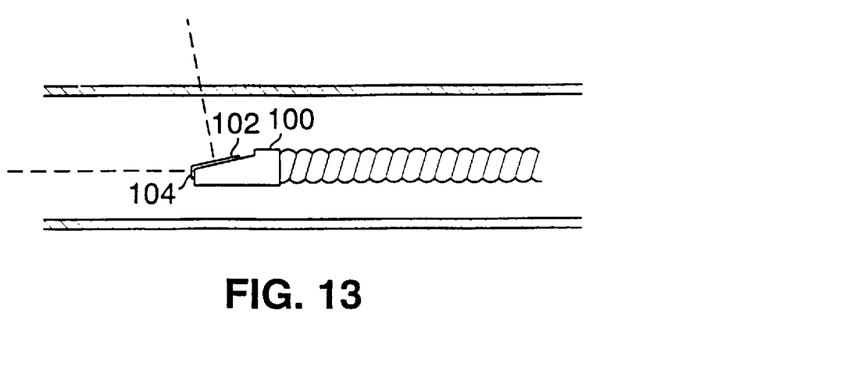

Referring to FIG. 13, in yet another embodiment, a single transducer may be used that emits ultrasonic energy in two spatially separate directions simultaneously. Transducer 100 includes facets 102 and 104. Facet 102 directs the ultrasonic signal substantially in a transverse direction, to obtain imaging information, whereas facet 104 directs ultrasonic energy axially, to obtain Doppler information.

In any of the above embodiments, the distal tip of the catheter may be opened or closed with a sonolucent material. The invention is applicable to use in body lumens other than blood vessels. For example, it may also be used as a transurethral probe to monitor the urine flow rate and lumen size. The beam directing embodiments can be implemented in various acoustic devices, such as guidewires, balloon catheters, and other probes of the type described, for example, in U.S. Pat. No. 4,951,677, issued Aug. 28, 1990; U.S. patent application Ser. No. 07/946,319, filed Aug. 21, 1990; U.S. patent application Ser. No. 07/946,809, filed Sep. 17, 1992; U.S. patent application Ser. No. 07/988,322, filed Dec. 9, 1992; and U.S. patent application Ser. No. 08/086,523, filed Jul. 1, 1993, the entire contents of all of which are hereby incorporated by reference. In addition any of the various features shown in the various embodiments described above may be combined together in a single device.

Still other embodiments are in the following claims.

What is claimed is:

1. A medical device for making Doppler measurements and imaging within a body fluid conduit using a single transducer, comprising:

an elongated device body defining a device axis and constructed for positioning a distal end of said device body near a region of interest in said body fluid conduit, and disposed within said device body, an ultrasonic beam-directing assembly constructed to direct a first portion of a given beam of ultrasonic energy from said single transducer in a direction for imaging within said body fluid conduit and to direct a second portion of said given beam of said ultrasonic energy in a different direction for making Doppler measurements within said body fluid conduit.

2. The device of claim 1 wherein said first portion of said ultrasonic energy is directed in a direction generally transverse to said device axis for imaging within said body fluid conduit and said second portion of said ultrasonic energy is directed in a direction generally along said device axis for making Doppler measurements within said body fluid conduit.

3. The device of claim 1 wherein said ultrasonic beam-directing assembly includes an ultrasonic beam splitter to spatially separate ultrasonic energy from said transducer into said first portion for providing an image of a wall of a body lumen and said second portion for making Doppler measurements of the flow of fluid in said body fluid conduit.

4. The device of claim 3 wherein said beam splitter is a partially sonolucent polymeric material spaced from said transducer in the path of said ultrasonic energy.

5. The device of claim 4 wherein said partially sonolucent polymeric material is located transversely with respect to said device axis.

6. The device of claim 4 wherein said partially sonolucent polymeric material forms at least a portion of the wall of said device body.

7. The device of claim 6 wherein the wall of said device body is shaped to efficiently direct said second portion of energy for making Doppler measurements generally along the axis of said device body.

8. The device of claim 7 wherein said device body has a flared distal end.

9. The device of claim 6 wherein said wall of said device body comprises angled ridges formed in a manner so as to gradually redirect said second portion of said ultrasonic energy generally along said device axis for making Doppler measurements within said body fluid conduit.

10. The device of claim 1 wherein said second portion of ultrasonic energy for making Doppler measurements is directed at an exit angle of 15° or less with respect to the device axis.

11. The device of claim 1 wherein the distal end of said device body is open.

12. The device of claim 1 wherein the distal end of said device body is closed and comprises sonolucent material.

13. The device of claim 12 constructed for varying the transmissivity and reflectivity of said beam-directing assembly by varying the acoustic impedance of said ultrasonic beam splitter.

14. The device of claim 13 constructed for varying the impedance of said ultrasonic beam splitter by flowing fluids of varying impedance behind said ultrasonic beam splitter.

15. The device of claim 13 constructed for varying impedance of said ultrasonic beam splitter by varying the thickness of a partially sonolucent beam directing material.

16. The device of claim 1 further comprising an analysis circuit that includes a timing circuit and a switch such that the ultrasonic imaging signal from said first portion of ultrasonic energy for imaging can be differentiated from the ultrasonic Doppler signal from said second portion of ultrasonic energy for making Doppler measurements by time delay between said signals, and said ultrasonic imaging signal and said Doppler signal can be separately analyzed by imaging and Doppler electronics.

17. The device of claim 1 wherein said beam directing assembly is an acoustically reflective ring disposed within said device body, a portion of said device body being formed from a sonolucent material.

18. The device of claim 1 wherein said transducer is mounted on a hinge constructed to permit said transducer to rotate between at least two angles.

19. The device of claim 1 wherein at least two facets are mounted on said transducer constructed to permit said transducer to emit ultrasonic energy in two spatially separate directions simultaneously.

20. The device of claim 1 wherein said first portion of ultrasonic energy and said second portion of ultrasonic energy are substantially perpendicular with respect to each other.

21. The device of claim 1 wherein the beam directing assembly is rotatable.

22. The device of claim 1 wherein said ultrasonic beam directing assembly is coupled to said transducer.

23. The device of claim 22 wherein said ultrasonic beam directing assembly and said transducer are both simultaneously rotatable.

24. A method for making Doppler measurements and imaging within a body fluid conduit, said method comprising the steps of:
  introducing a medical device into a patient's body fluid conduit, said medical device including an ultrasonic transducer and an ultrasonic beam-directing assembly near the distal end of said device;
  positioning said distal end near a region of interest within said body fluid conduit;
  directing ultrasonic energy from said transducer to said beam-directing assembly for directing a first portion of said energy in a first direction for imaging within said body fluid conduit and for simultaneously directing a second portion of said energy in a second, different direction for making Doppler measurements within said body fluid conduit; and
  receiving the reflected energy back containing the image and flow information.

25. A method as in claim 24 wherein the ultrasonic beamdirecting assembly is an ultrasonic beam splitter which spatially separates said ultrasonic energy from said transducer into a first portion for providing an image of a wall of said body fluid conduit and a second portion for making Doppler measurements of the flow of fluid in said body fluid conduit.

* * * * *

UNITED STATES PATENT AND TRADEMARK OFFICE
CERTIFICATE OF CORRECTION

PATENT NO. : 6,074,349
DATED : June 13, 2000
INVENTOR(S) : Robert J. Crowley

It is certified that error appears in the above-identified patent and that said Letters Patent is hereby corrected as shown below:

In column 10, line 20, please change "beamdirecting" to -- beam-directing --.

Signed and Sealed this

Eighth Day of May, 2001

Attest:

NICHOLAS P. GODICI

Attesting Officer     Acting Director of the United States Patent and Trademark Office